(12) United States Patent
Fischer et al.

(10) Patent No.: US 7,452,209 B2
(45) Date of Patent: Nov. 18, 2008

(54) EXOSKELETON SUPPORT FOR PLACEMENT OF A DENTAL TREATMENT STRIP

(75) Inventors: Dan E. Fischer, Sandy, UT (US); Bruce S. McLean, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 633 days.

(21) Appl. No.: 11/120,112

(22) Filed: May 2, 2005

(65) Prior Publication Data

US 2006/0246400 A1 Nov. 2, 2006

(51) Int. Cl.
*A61C 5/00* (2006.01)
*A61K 6/02* (2006.01)

(52) U.S. Cl. .................................. 433/216; 433/80

(58) Field of Classification Search ............... 433/37, 433/45, 47, 80, 215, 216
See application file for complete search history.

(56) References Cited

U.S. PATENT DOCUMENTS

| | | | |
|---|---|---|---|
| 165,854 A | 7/1875 | Hopfen | |
| 1,637,153 A | 7/1927 | Lawton | |
| 2,092,097 A | 9/1937 | Town | |
| 2,257,709 A | 9/1941 | Anderson | |
| 2,835,628 A | 5/1958 | Saffir | |
| 3,339,547 A | 9/1967 | Drabkowski | |
| 3,527,219 A | 9/1970 | Greenberg | |
| 3,577,640 A | 5/1971 | Lee | |
| 3,624,909 A | 12/1971 | Greenberg | |
| 3,688,406 A | 9/1972 | Porter et al. | |
| 3,955,281 A | 5/1976 | Weitzman | |
| 4,044,762 A | 8/1977 | Jacobs | |
| 4,063,552 A * | 12/1977 | Going et al. | 128/861 |
| 4,064,628 A | 12/1977 | Weitzman | |
| 4,138,814 A | 2/1979 | Weitzman | |
| RE33,093 E | 10/1989 | Schiraldi et al. | |

(Continued)

FOREIGN PATENT DOCUMENTS

WO 8806869 9/1988

(Continued)

OTHER PUBLICATIONS

Technical Bulletin: Hydrogen Peroxide-Polyvinylpyrrolidone Polymer Complexes, International Specialty Products, 1361 Alps Road, Wayne New Jersey 07470, www.ispcorp.com (Dec. 2003).
Office Action dated Sep. 21, 2004 cited in related U.S. Appl. No. 10/444,242.
Notice of Allowance dated Sep. 16, 2005 cited in related U.S. Appl. No. 10/444,242.
Office Action dated Feb. 8, 2006 cited in related U.S. Appl. No. 11/047,150.

(Continued)

*Primary Examiner*—Ralph A Lewis
(74) *Attorney, Agent, or Firm*—Workman Nydegger

(57) ABSTRACT

An exoskeleton support and associated placement system for use in placing a thin, flexible dental treatment strip over a person's tooth surfaces. The exoskeleton support includes an exoskeleton body that is curved so as to approximate the curvature of a person's dental arch. The exoskeleton support includes an inner surface that is oriented toward a person's tooth surfaces during use, an outer surface oriented away from the person's tooth surfaces during use, and means for temporarily holding or attaching a flexible dental treatment strip to the inner surface of the exoskeleton support. The exoskeleton support allows a user to more easily and accurately place a dental treatment strip on tooth surfaces to be treated.

15 Claims, 4 Drawing Sheets

U.S. PATENT DOCUMENTS

| | | |
|---|---|---|
| 4,900,721 A | 2/1990 | Bansemir et al. |
| 4,902,227 A | 2/1990 | Smith |
| 5,008,093 A | 4/1991 | Merianos |
| 5,051,476 A | 9/1991 | Uji et al. |
| 5,059,120 A | 10/1991 | Lee |
| 5,076,791 A | 12/1991 | Madray, Jr. |
| 5,085,585 A | 2/1992 | Zimble |
| 5,108,742 A | 4/1992 | Merianos |
| 5,112,225 A | 5/1992 | Diesso |
| 5,165,424 A | 11/1992 | Silverman |
| 5,183,901 A | 2/1993 | Login et al. |
| 5,211,559 A | 5/1993 | Hart et al. |
| 5,310,563 A | 5/1994 | Curtis et al. |
| 5,326,685 A | 7/1994 | Gaglio et al. |
| 5,346,061 A | 9/1994 | Newman et al. |
| 5,356,291 A | 10/1994 | Darnell |
| 5,370,533 A | 12/1994 | Bushnell |
| 5,376,006 A | 12/1994 | Fischer |
| 5,425,953 A | 6/1995 | Sintov et al. |
| 5,460,527 A | 10/1995 | Kittelsen |
| 5,562,449 A | 10/1996 | Jacobs et al. |
| 5,573,399 A | 11/1996 | McClintock, II |
| 5,575,654 A | 11/1996 | Fontenot |
| 5,611,687 A | 3/1997 | Wagner |
| 5,616,027 A | 4/1997 | Jacobs et al. |
| 5,631,000 A | 5/1997 | Pellico et al. |
| 5,639,445 A | 6/1997 | Curtis et al. |
| 5,702,251 A | 12/1997 | McClintock, II |
| 5,707,235 A | 1/1998 | Knutson |
| 5,711,935 A | 1/1998 | Hill et al. |
| 5,752,826 A | 5/1998 | Andreiko |
| 5,769,633 A | 6/1998 | Jacobs et al. |
| 5,816,802 A | 10/1998 | Montgomery |
| 5,846,058 A | 12/1998 | Fischer |
| 5,851,512 A | 12/1998 | Fischer |
| 5,863,202 A | 1/1999 | Fontenot et al. |
| 5,879,691 A | 3/1999 | Sagel et al. |
| 5,891,453 A | 4/1999 | Sagel et al. |
| 5,894,017 A | 4/1999 | Sagel et al. |
| 5,895,218 A | 4/1999 | Quinn et al. |
| 5,922,307 A | 7/1999 | Montgomery |
| 5,924,863 A | 7/1999 | Jacobs et al. |
| 5,980,249 A | 11/1999 | Fontenot |
| 5,985,249 A | 11/1999 | Fischer |
| 5,989,569 A | 11/1999 | Dirksing et al. |
| 6,045,811 A | 4/2000 | Dirksing et al. |
| 6,080,397 A | 6/2000 | Pfirrmann |
| 6,089,869 A | 7/2000 | Schwartz |
| 6,096,328 A | 8/2000 | Sagel et al. |
| 6,106,293 A | 8/2000 | Wiesel |
| 6,126,443 A | 10/2000 | Burgio |
| 6,136,297 A | 10/2000 | Sagel et al. |
| 6,142,780 A | 11/2000 | Burgio |
| 6,155,832 A | 12/2000 | Wiesel |
| 6,183,251 B1 | 2/2001 | Fischer |
| 6,197,331 B1 | 3/2001 | Lerner et al. |
| 6,247,930 B1 | 6/2001 | Chiang et al. |
| 6,274,122 B1 | 8/2001 | McLaughlin |
| 6,277,458 B1 | 8/2001 | Dirksing et al. |
| 6,280,196 B1 | 8/2001 | Berghash |
| 6,287,120 B1 | 9/2001 | Wiesel |
| 6,309,625 B1 | 10/2001 | Jensen et al. |
| 6,312,671 B1 | 11/2001 | Jensen et al. |
| 6,322,360 B1 | 11/2001 | Burgio |
| 6,331,292 B1 | 12/2001 | Montgomery |
| 6,343,932 B1 | 2/2002 | Wiesel |
| 6,364,665 B1 | 4/2002 | Trettenero |
| 6,379,147 B1 | 4/2002 | Georgakis et al. |
| 6,382,979 B2 | 5/2002 | Lindquist |
| 6,419,903 B1 | 7/2002 | Xu et al. |
| 6,419,906 B1 | 7/2002 | Xu et al. |
| 6,435,873 B1 | 8/2002 | Burgio |
| 6,440,396 B1 | 8/2002 | McLaughlin |
| 6,458,380 B1 | 10/2002 | Leaderman |
| 6,461,158 B1 | 10/2002 | Sagel et al. |
| 6,488,914 B2 | 12/2002 | Montgomery |
| 6,497,575 B2 | 12/2002 | Zavitsanos et al. |
| 6,500,408 B2 | 12/2002 | Chen |
| 6,503,486 B2 | 1/2003 | Xu et al. |
| 6,506,053 B2 | 1/2003 | Wiesel |
| 6,514,483 B2 | 2/2003 | Xu et al. |
| 6,514,484 B2 | 2/2003 | Rajaiah et al. |
| 6,551,579 B2 | 4/2003 | Sagel et al. |
| 6,607,382 B1 | 8/2003 | Kuo et al. |
| 6,638,496 B2 | 10/2003 | McLaughlin |
| 6,649,147 B1 | 11/2003 | Ye et al. |
| 6,682,721 B2 | 1/2004 | Kim et al. |
| 6,689,344 B2 | 2/2004 | Chang et al. |
| 6,730,316 B2 | 5/2004 | Chen |
| 7,040,897 B2 * | 5/2006 | Fischer et al. ............... 433/216 |
| 7,059,858 B2 * | 6/2006 | McLean et al. ............. 433/216 |
| 7,070,413 B1 * | 7/2006 | Wagner ..................... 433/214 |
| 7,114,953 B1 * | 10/2006 | Wagner ..................... 433/214 |
| 7,247,022 B2 * | 7/2007 | Allred et al. ................ 433/216 |
| 2001/0046654 A1 | 11/2001 | Zavitsanos et al. |
| 2002/0006387 A1 | 1/2002 | Sagel et al. |
| 2002/0006388 A1 | 1/2002 | Sagel et al. |
| 2002/0012685 A1 | 1/2002 | Sagel et al. |
| 2002/0018754 A1 | 2/2002 | Sagel et al. |
| 2002/0081555 A1 | 6/2002 | Wiesel |
| 2002/0164292 A1 | 11/2002 | Peterson et al. |
| 2002/0182154 A1 | 12/2002 | McLaughlin |
| 2002/0187111 A1 | 12/2002 | Xu et al. |
| 2002/0187112 A1 | 12/2002 | Xu et al. |
| 2003/0003421 A1 | 1/2003 | Besenheider et al. |
| 2003/0012747 A1 | 1/2003 | Peterson |
| 2003/0036037 A1 | 2/2003 | Zavitsanos et al. |
| 2003/0044631 A1 | 3/2003 | Sagal et al. |
| 2003/0068284 A1 | 4/2003 | Sagel et al. |
| 2003/0068601 A1 | 4/2003 | Zavitsanos et al. |
| 2003/0082114 A1 | 5/2003 | Kim et al. |
| 2003/0133884 A1 | 7/2003 | Chang et al. |
| 2003/0152884 A1 | 8/2003 | Wiechmann et al. |
| 2003/0194382 A1 | 10/2003 | Chang et al. |
| 2003/0198606 A1 | 10/2003 | Kim et al. |
| 2004/0002034 A1 | 1/2004 | Jacobs et al. |
| 2004/0002035 A1 | 1/2004 | Jacobs et al. |
| 2004/0038183 A1 | 2/2004 | Jacobs et al. |
| 2004/0146836 A1 | 7/2004 | Andersen |
| 2004/0146837 A1 | 7/2004 | Andersen |
| 2004/0214140 A1 | 10/2004 | Fischer et al. |
| 2004/0234929 A1 | 11/2004 | Fischer et al. |
| 2004/0241618 A1 | 12/2004 | Allred et al. |
| 2004/0242620 A1 | 12/2004 | Allred et al. |
| 2005/0186150 A1 | 8/2005 | Allred et al. |
| 2005/0186539 A1 | 8/2005 | McLean et al. |
| 2005/0249667 A1 | 11/2005 | Tuszynski et al. |

FOREIGN PATENT DOCUMENTS

| | | |
|---|---|---|
| WO | 03000216 A1 | 1/2003 |

OTHER PUBLICATIONS

Notice of Allowance dated Apr. 27, 2007 cited in related U.S. Appl. No. 11/047,150.

Office Action dated Jun. 12, 2006 cited in related U.S. Appl. No. 10/719,105.

Office Action dated Apr. 5, 2005 cited in related U.S. Appl. No. 10/783,597.

Office Action dated Apr. 20, 2006 cited in related U.S. Appl. No. 10/962,884.

* cited by examiner

EXOSKELETON SUPPORT FOR PLACEMENT OF A DENTAL TREATMENT STRIP

BACKGROUND OF THE INVENTION

1. The Field of the Invention

The present invention is in the field of dental treatment systems that include dental strips used in applying a dental bleach, fluoride, desensitizing agent, antimicrobial agent, anticariogenic agent, or other dental agents to a person's teeth and/or gums. More particularly, the invention relates to placement systems for placing a thin, flexible dental treatment strip over a person's tooth and/or gum surfaces.

2. The Relevant Technology

Virtually all people desire white or whiter teeth. To achieve this goal, people either have veneers placed over their teeth or have their teeth chemically bleached. In the past, people who desired to have their teeth bleached had to submit to conventional in-office bleaching techniques. The process generally involves: (1) making an alginate impression of the patient's teeth; (2) making a stone cast or model of the impression; (3) vacuum forming a dental tray from the model, usually from a sheet of thin ethyl vinyl acetate (EVA) material, and trimming to exclude gingival coverage. This method results in a tray that is soft and flexible and that is very accurately customized to the patient's teeth. However, the method is time consuming and the resulting tray is relatively expensive.

Because of the high cost of producing custom dental trays, less costly alternatives have been developed. One such alternative is a strip of a flexible plastic material coated with a bleaching agent that can be applied to a user's teeth. Such strips are placed against the teeth by the user to cover the labial surface of at least some of the front teeth (e.g., 6-8 teeth) and then folded back to cover the occlusal surface and possibly a portion of the lingual surfaces. Because the dental strips are often very thin and flexible, they can be awkward to place correctly. In many cases, they will fold together and self adhere or become mangled before being properly placed over a person's teeth. Because of this difficulty, replacement and refitting of the strips is often required.

In view of the foregoing, there is an ongoing need for a dental treatment system that would allow a person to more easily and accurately place a dental strip over teeth to be treated.

BRIEF SUMMARY OF THE PREFERRED EMBODIMENTS

The present invention is directed to an exoskeleton support for use in placing a thin, flexible dental treatment strip over a person's tooth surfaces. The exoskeleton support includes a curved body so as to approximate the curvature of a person's dental arch. The exoskeleton support includes an inner surface oriented toward a person's teeth during use, and an outer surface oriented away from the person's tooth surfaces during use. The exoskeleton support also includes means for temporarily holding or attaching a flexible dental treatment strip to the inner surface of the exoskeleton body. The exoskeleton support allows a user to more easily and accurately place a dental treatment strip on a tooth surface to be treated.

In one example, the exoskeleton support may further include a handle (e.g., formed on the outer surface of the exoskeleton body) that facilitates a user gripping and maneuvering the exoskeleton body during use.

The exoskeleton support may be formed of any suitable material and may be semi-rigid, rigid, or flexible. Suitable materials for making the exoskeleton body include, for example, polyurethane, an elastomer, a molded/thermoformed plastic, a shapeable plastic, closed or open cell polymeric foam, metal (e.g., stamped or formed), wire, cardboard, paraffin wax, or any other suitable material.

According to one embodiment, the means for temporarily holding or attaching a flexible dental treatment strip to the inner surface of the exoskeleton body may comprise any suitable sticky or adhesive material. Suitable examples include, but are not limited to glycerin, polyethylene glycol, an adhesive silicon, petrolatum, oils (e.g., mineral oil), a tackifying sweetener (e.g., honey), sticky polymers in water or another solvent (e.g., glycerin or a glycol), or a sticky resin.

In another example, the means for temporarily holding or attaching the flexible dental treatment strip to the exoskeleton body may comprise a static attraction (i.e., static cling) between the exoskeleton body material and the material of the dental treatment strip.

The invention also provides a placement system that includes an exoskeleton support as described above and a flexible dental treatment strip. The strip is removably attached to the inner surface of the exoskeleton body.

The flexible dental treatment strip of the placement system may include a dental treatment composition (e.g., a sticky dental bleaching composition) adjacent to an inner surface of the strip. Other dental treatment compositions may include desensitizing compositions, fluoride compositions, antimicrobial compositions, and anticariogenic compositions.

The exoskeleton support and dental treatment strip of the placement system may be conveniently pre-packaged together e.g., in a foil pouch, under a peelable cover, or in other packaging capable of keeping a dental treatment composition from drying out or otherwise being inactivated or contaminated. In order to use a pre-packaged placement system, the user removes the placement system from the packaging and places it so that the flexible dental treatment strip covers at least a portion of the user's upper or lower teeth. The exoskeleton support is used to support the treatment strip while the user maneuvers the placement system into place. Once the dental treatment strip has been placed as desired, the exoskeleton support is separated from the dental strip. Because the dental treatment strip is coated with a sticky or adhesive treatment composition, once placed over the teeth, the sticky or adhesive treatment composition holds the strip against the teeth in the absence of the exoskeleton support.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The invention relates to exoskeleton supports and related placement systems for use in placing a thin, flexible dental treatment strip over a person's tooth surfaces. The exoskeleton support includes a curved body so as to approximate the curvature of a person's dental arch. The exoskeleton support includes an inner surface for placement against a person's tooth surfaces, and an outer surface oriented away from the person's tooth surfaces during use. The exoskeleton tray support includes means for temporarily holding or attaching a flexible dental treatment strip to the inner surface of the exoskeleton body.

The exoskeleton support and associated placement system allow a user to more easily and accurately place a dental treatment strip on a tooth surface to be treated. The inventive placement system and exoskeleton support can be used for placing a dental treatment strip used for any desired dental treatment, such as tooth bleaching, desensitizing, fluoride treatments, antimicrobial treatments, and/or anticariogenic treatments.

II. Exemplary Exoskeleton Supports and Placement Systems

Figure 1A:
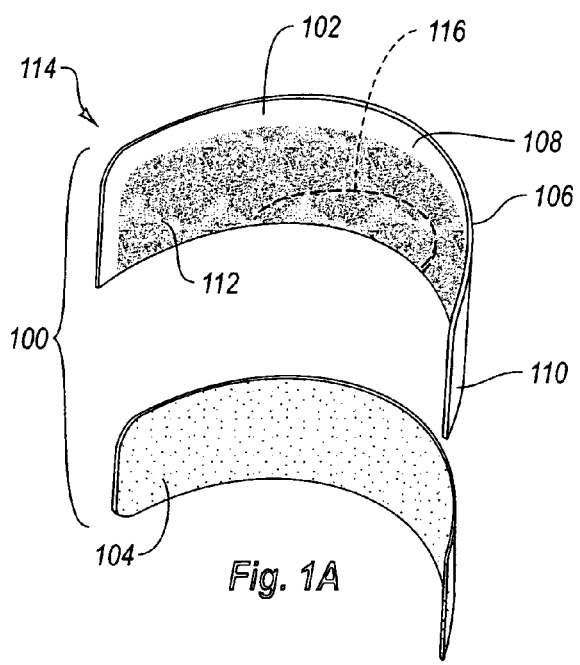
FIG. 1A is an exploded view of an exemplary placement system including an exoskeleton support and a dental treatment strip.

FIG. 1A depicts (in exploded view) an exemplary placement system 100 including an exoskeleton body 102 that may be used in placing a flexible dental treatment strip 104 over a person's teeth. The exoskeleton support body 102 has a curved body so as to approximate the curvature of a person's dental arch. In the illustrated embodiment the exoskeleton support body 102 comprises a wall 106 including an inner surface 108 for placement against a person's tooth surfaces and an outer surface 110 oriented away from the person's tooth surfaces during placement.

As illustrated, placement device 100 also includes means for temporarily holding or attaching flexible dental treatment strip 104 to the inner surface 108 of exoskeleton support body 102. According to one embodiment, the means for temporarily holding or attaching dental strip 104 to the body 102 may comprise any suitable sticky or adhesive material 112. Suitable examples include, but are not limited to glycerin, polyethylene glycol, an adhesive silicon, petrolatum, oils (e.g., mineral oil), tackifying sweeteners (e.g., honey), sticky polymers in water or another solvent (e.g., glycerin or a glycol), or a sticky resin.

Alternatively, the means for temporarily holding or attaching the flexible dental treatment strip may comprise a static attraction (i.e., static cling) between the material of exoskeleton support body 102 and the material of the dental treatment strip 104.

The sticky or adhesive materials may be hydrophobic or water soluble, as desired. A hydrophobic material may more easily spread over the inner surface 108 of the exoskeleton body 102 and the adjacent surface of the dental treatment strip. A water soluble material may be more easily removed from the exposed surface of the strip, e.g., by rinsing, after placement over the teeth and removal of the exoskeleton body.

In this embodiment, exoskeleton support tray 114 comprises both exoskeleton body 102 and means for temporarily holding or attaching (e.g., sticky or adhesive material 112 to the body 102). An exemplary exoskeleton support 114 is perhaps best seen in FIG. 1A, the figure illustrating placement device 100 in an exploded configuration.

Figure 3:
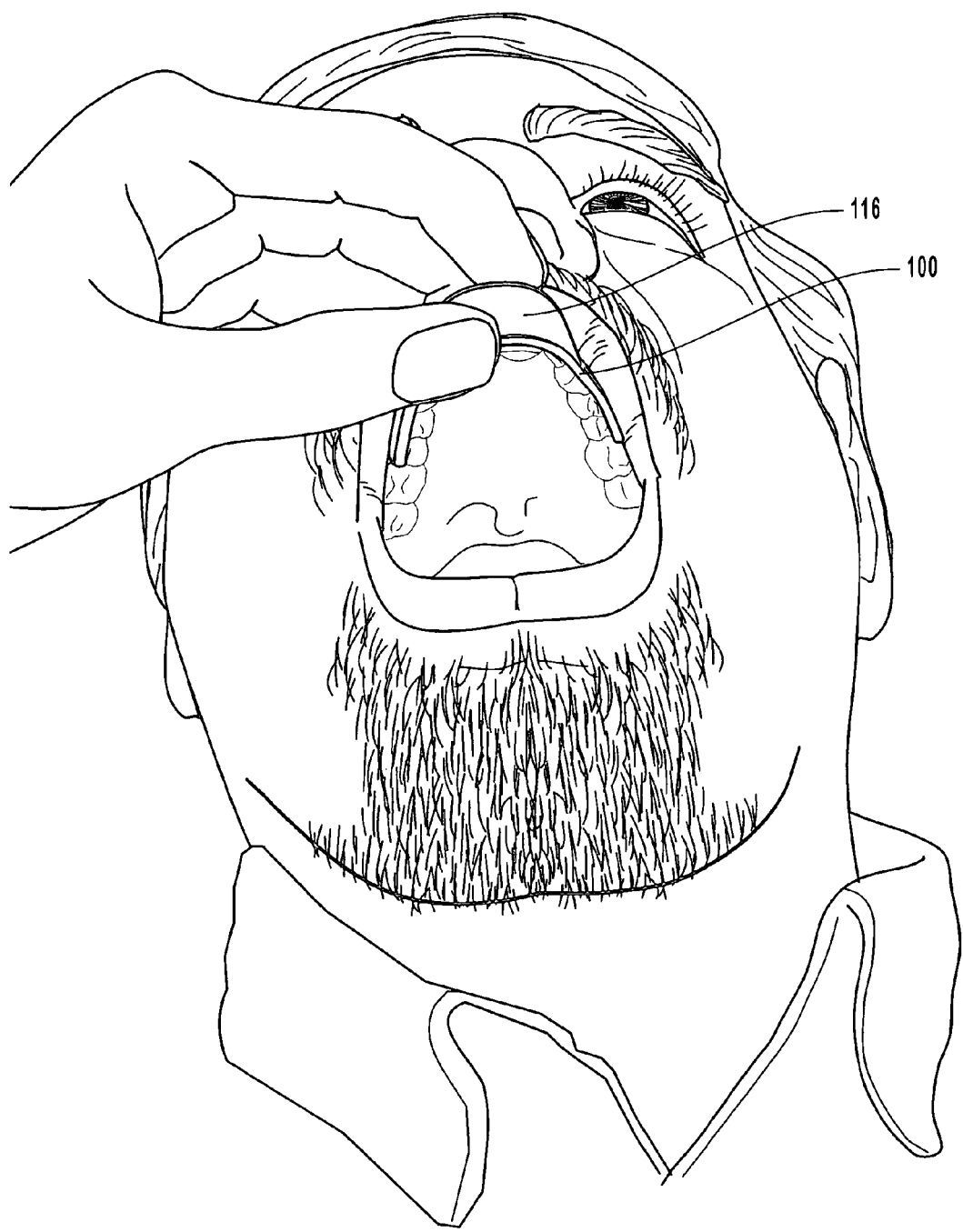
FIG. 3 illustrates a placement system being used to place a dental treatment strip over a person's teeth.

As illustrated, exoskeleton support 114 may also include an optional handle 116 (perhaps best seen in FIG. 3). The handle 116 facilitates placement of the placement system 100 over a person's teeth by providing a structure that can be more easily gripped. It also facilitates easy removal of the exoskeleton body 102 once the dental treatment strip 104 is adhered to the person's teeth.

In one embodiment, handle 116 may be located at or near the top or bottom edge (depending on system orientation) of wall 106. In such an arrangement, easy placement may be facilitated when the system is oriented such that the handle is disposed towards the occlusal surface of the person's teeth. This minimizes interference between the handle 116 and the lips of the person during placement. In order to place the system over the opposite dental arch (e.g., the bottom dental arch), the placement system may simply be flipped over so as to orient the handle towards the occlusal surface and minimize interference between the handle and the person's lips.

Figure 1B:
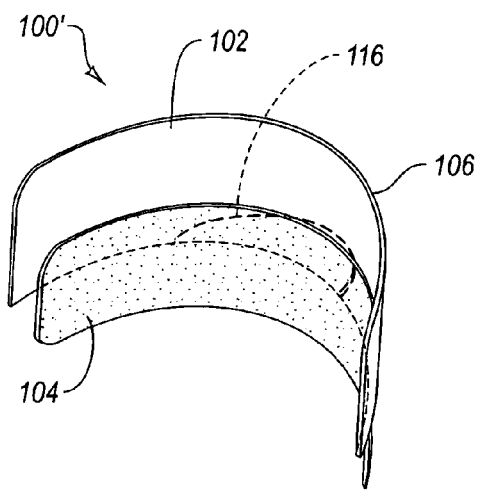
FIG. 1B is an assembled perspective view of an alternative placement system including an exoskeleton support and a dental treatment strip.

FIG. 1B illustrates an alternative placement system 100' that includes an exoskeleton body 102, dental treatment strip 104, and may include means for temporarily holding or attaching strip 104 to exoskeleton body 102 (e.g., a sticky or adhesive material). Similar to placement system 100, exoskeleton body 102 includes a wall 106 and a handle 116. Dental treatment strip 104 is attached to exoskeleton body 102 so that at least a portion of strip 104 remains unattached (i.e., hangs free) to exoskeleton body 102. Such a configuration allows a user to place the system 100' over the tooth surfaces to be treated, and then fold the unattached portion of dental treatment strip 104 over the occlusal edge of the tooth surfaces to be treated, without first requiring removal of exoskeleton body 102. Depending on the width of the unattached portion of dental strip 104, this portion may be further folded to cover at least a portion of the lingual surface of the tooth surfaces to be treated.

In one embodiment, the optional handle may be located at or near the top or bottom edge (depending on system orientation) of wall 106. In such an arrangement, easy placement may be facilitated when the system is oriented such that the handle is disposed towards the occlusal surface of the person's teeth. This minimizes interference between the handle and the lips of the person during placement. In order to place the system 100' over the opposite dental arch (e.g., the bottom dental arch), the placement system may simply be flipped over so as to orient the handle towards the occlusal surface and minimize interference between the handle and the person's lips.

Figure 1C:
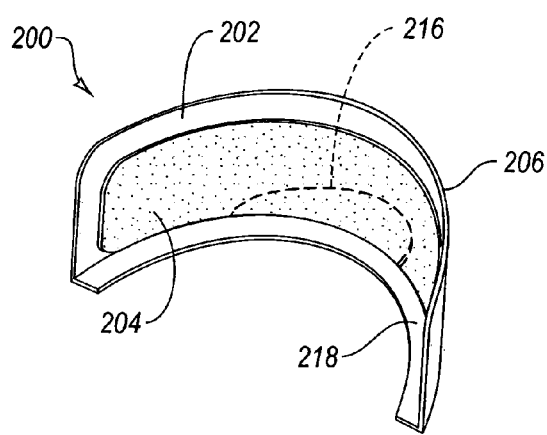
FIG. 1C is a perspective view of another alternative exemplary placement system including an exoskeleton support and a dental treatment strip.

FIG. 1C illustrates an alternative placement system 200 that includes an alternative exoskeleton support body 202, a dental treatment strip 204, and means for temporarily holding or attaching strip 204 to exoskeleton body 202 (e.g., a sticky or adhesive material). Alternative exoskeleton support body 202 includes a front wall 206, a bottom wall 218, and a handle 216. The inclusion of bottom wall 218 gives exoskeleton body 202 an "L" shaped cross section. Inclusion of bottom wall 218 helps retain dental treatment strip 204 in place by preventing disruption of the strip 204 as the person maneuvers the placement system 200 as desired. Thus, bottom wall 218 comprises means for temporarily holding or attaching a strip to an exoskeleton support.

In one embodiment, the optional handle may be located at or near the top or bottom edge (depending on system orientation) of front wall 206. In such an arrangement, easy placement may be facilitated when the system is oriented such that the handle is disposed towards the occlusal surface of the person's teeth. This minimizes interference between the handle and the lips of the person during placement. In order to place the system 200 over the opposite dental arch (e.g., the bottom dental arch), the placement system may simply be flipped over so as to orient the handle towards the occlusal surface and minimize interference between the handle and the person's lips.

Figure 1D:
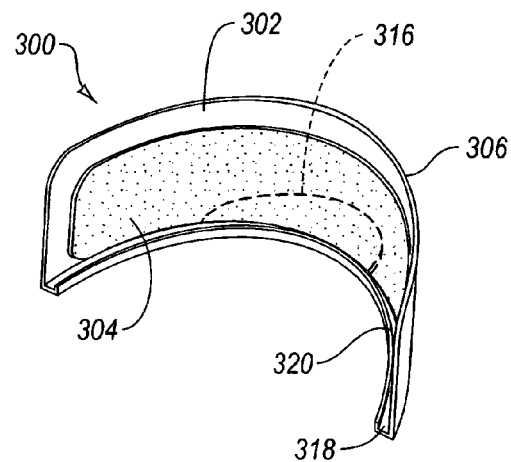
FIG. 1D is a perspective view of another alternative exemplary placement system including an exoskeleton support and a dental treatment strip.

FIG. 1D illustrates another alternative placement system 300 that includes exoskeleton support body 302, a dental treatment strip 304, and means for temporarily holding or attaching strip 304 to exoskeleton body 302 (e.g., a sticky or adhesive material). Exoskeleton body 302 includes a front wall 306, a bottom wall 318, a rear wall 320, and a handle 316. The inclusion of bottom wall 318 and rear wall 320 gives exoskeleton body 302 an approximate "U" shaped cross section. The relative lengths of front wall 306, bottom wall 318, and rear wall 320 may be as desired. Inclusion of bottom wall 318 and rear wall 320 help retain dental treatment strip 304 in place by preventing disruption of the strip 304 as the person maneuvers the placement system 300 as desired. They therefore comprise means of temporarily holding or attaching a strip to an exoskeleton support.

In one embodiment, the optional handle may be located at or near the top or bottom edge (depending on system orientation) of front wall 306. In such an arrangement, easy placement may be facilitated when the system is oriented such that the handle is disposed towards the occlusal surface of the person's teeth. This minimizes interference between the handle and the lips of the person during placement. In order to place the system 300 over the opposite dental arch (e.g., the bottom dental arch), the placement system may simply be flipped over so as to orient the handle towards the occlusal surface and minimize interference between the handle and the person's lips.

The exoskeleton support may be formed of any suitable material. Exemplary materials include, but are not limited to polyurethane, an elastomer, molded/thermoformed plastic, a shapeable plastic, a light activated shape memory polymer, closed or open cell polymeric foam, metal (e.g., stamped or formed), wire, cardboard, paraffin wax, or any other suitable material.

Non-limiting examples of some specific suitable plastics include ultra low density polyethylene (ULDPE), low density polyethylene, ethylene-vinyl acetate (EVA) copolymer, polycaprolactone (PCL), polyethylene, polypropylene, or polyvinyl chloride (PVC). Flow additives, plasticizers, and fillers may be added as desired.

Examples of suitable ULDPE materials include various polymers sold under the general trade name Attaneg® by Dow Chemical. Another suitable ULDPE material is Exact® 4041 made by Exxon-Mobil Chemical. An example of a suitable EVA material is Elvax® 250, available from Dupont. An example of a suitable PCL material is Capra®650 from Solvoy-Interox. An example of a suitable polyethylene material, which is also a shapeable plastic, is FORTE STRIP from Sekisui Chemical Co. Ltd. An example of a suitable light activated shape memory polymer has been jointly developed by RWTH in Aachen, Germany and MIT in Cambridge, Mass. Other materials and blends useful in making exoskeleton bodies are disclosed in U.S. Pat. No. 5,769,633 to Jacobs et al., U.S. Pat. No. 5,051,476 to Uji et al., and U.S. Pat. No. 6,089,869 to Schwartz. For purposes of disclosing materials that can be made into exoskeleton bodies, the foregoing patents are incorporated herein by reference.

Figure 2:
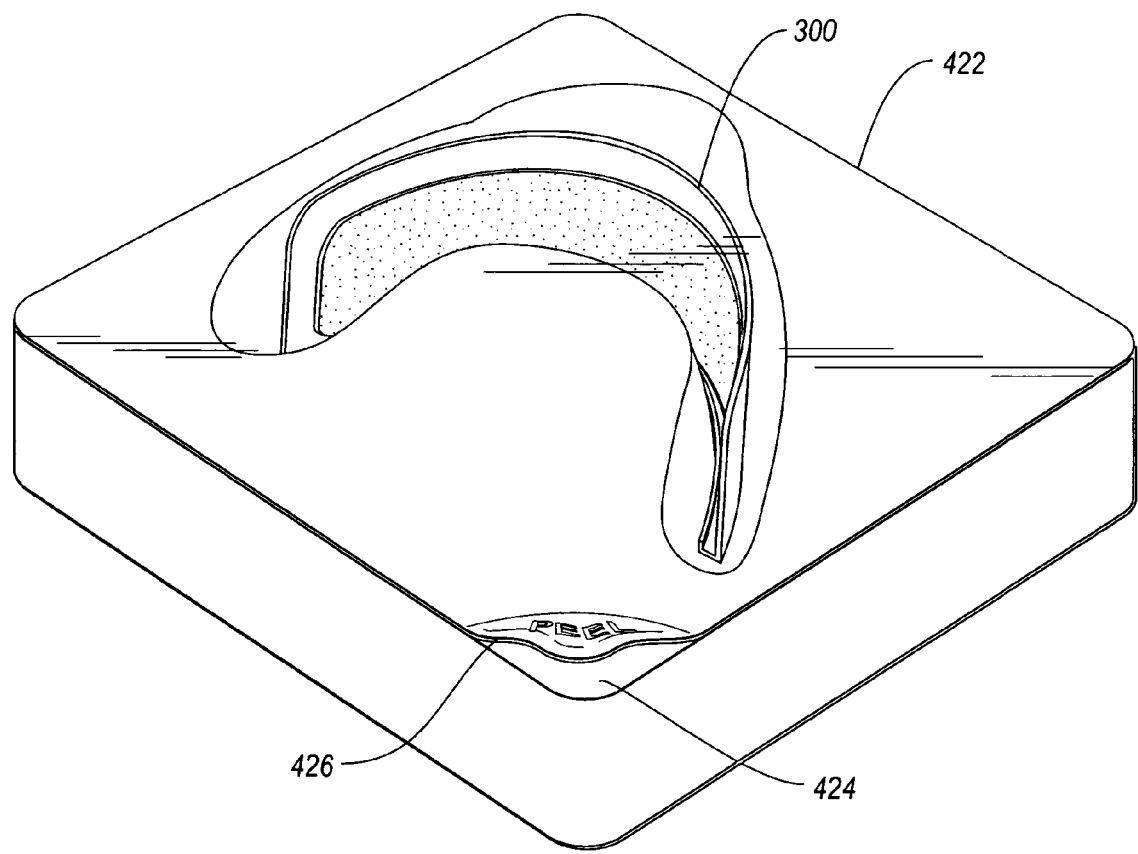
FIG. 2 is a perspective view of an exemplary placement system including an exoskeleton support and a dental treatment strip packaged within a container.

As illustrated in FIG. 2, a placement system according to the invention (e.g., placement system 300) can be sealed within a protective package 422 that includes a rigid support layer 424 and a peelable cover 426. When it is desired to use the placement system 300, the peelable cover 426 is removed and the placement system 300 is removed or separated from the support layer 424.

Although illustrated as packaged within a sealed package, it is to be understood that any placement system may alternatively be packaged within a plastic or foil pouch.

The placement systems according to the invention may be provided in a kit including a plurality of dental treatment strips and at least one exoskeleton body. Such a kit allows a user to reuse the exoskeleton body.

In use, both the dental bleaching strip and exoskeleton support are placed into a person's mouth so as to initially position the strip 104 over the person's teeth as desired. The exoskeleton may include a handle to facilitate placement and positioning within the mouth. Thereafter, the exoskeleton support is removed, leaving only the dental treatment strip within the person's mouth. Further manipulation (e.g., fine adjustments) of the strip may be performed once the exoskeleton support has been removed, if desired.

FIG. 3 depicts a person using a placement system 100 to place a dental treatment strip over the person's teeth. The exoskeleton support temporarily maintains treatment strip in its original shape so as to facilitate placement of the strip over the person's teeth. The exoskeleton support provides an advantage over attempting to place a flexible dental treatment strip without the assistance of an exoskeleton support. Once the flexible treatment strip has been placed over the person's teeth, the exoskeleton support is removed so that only the treatment strip containing the treatment composition remains over the person's teeth.

Figure 4:
FIG. 4 illustrates a dental treatment strip after it has been placed over a person's teeth and the exoskeleton support removed.

FIG. 4 illustrates a dental treatment strip 104 placed over the person's teeth after the exoskeleton body has been removed. The illustrated strip 104 has been folded over the occlusal and a portion of the lingual surface of the teeth to be treated. Whether the occlusal and lingual tooth surfaces are covered simply depends on the width and placement of the strip 104. The illustrated dental treatment strip 104 covers the eight front teeth, although the strip could be configured to treat more or fewer teeth, as desired.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental treatment system for use in applying a treatment composition to a person's teeth, comprising:

a generally flat, elongated dental treatment strip which is thin and flexible, and which is coated with a sticky or adhesive treatment composition so that when placed onto a portion of a person's upper or lower dental arch the treatment composition will hold the strip against the teeth in the absence of heating it to form it, or placing any other structure over it;

an exoskeleton body that is comprised of a flat, curved wall so as to approximate the curvature of a person's upper or lower dental arch, the exoskeleton body including an inner surface of the flat, curved wall that is oriented towards a person's tooth surfaces when used to place the dental treatment strip onto a person's teeth, and an outer surface oriented away from the person's tooth surfaces during placement of the dental treatment strip; and means for temporarily holding or attaching the flexible dental treatment strip to the inner surface of the flat, curved wall of the exoskeleton body until the dental treatment strip is placed onto a portion of the person's teeth, so that thereafter the dental treatment strip will be held to the teeth without any other structure while the exoskeleton body is removed from the dental treatment strip.

2. A dental treatment system as recited in claim 1, wherein the means for temporarily holding or attaching a flexible dental treatment strip to the inner surface of the exoskeleton body comprises a sticky or adhesive material.

3. A dental treatment system as recited in claim 2, wherein the sticky or adhesive material comprises at least one member selected from the group consisting of glycerin, polyethylene glycol, adhesive silicon, petrolatum, oils, tackifying sweeteners, sticky polymers in water or another solvent, and sticky resins.

4. A dental treatment system as recited in claim 1, wherein the means for temporarily holding or attaching a flexible dental treatment strip to the inner surface of the exoskeleton body comprises a static attraction between the exoskeleton body material and the material of the dental treatment strip.

5. A dental treatment system as recited in claim 1, further comprising a handle that facilitates a user gripping and maneuvering the exoskeleton body during use.

6. A dental treatment system as recited in claim 1, wherein the exoskeleton body comprises at least one of polyurethane, an elastomer, a molded or thermoformed plastic, closed or open cell polymeric foam, metal, wire, cardboard, or paraffin wax.

7. A dental treatment system as recited in claim 1, wherein the exoskeleton body comprises a shapeable plastic.

8. A dental treatment system as recited in claim 1, wherein the exoskeleton body comprises a light activated shape memory polymer.

9. A dental treatment system as recited in claim 8, wherein the flexible dental treatment strip includes a dental treatment composition adjacent to an inner surface of the strip.

10. A dental treatment system as recited in claim 9, wherein the dental treatment composition comprises at least one of a dental bleaching agent, an anticariogenic agent, an antimicrobial agent, a remineralizing agent, a desensitizing agent, or fluoride.

11. A dental treatment system as recited in claim 9, wherein the exoskeleton body and dental treatment strip including a dental treatment composition are contained within a sealed package.

12. A dental treatment system as recited in claim 11, wherein the sealed package comprises at least one of a plastic or foil pouch.

13. A dental treatment system as recited in claim 11, wherein the sealed package comprises a peelable cover.

14. A dental treatment system as defined in claim 11 further comprising a plurality of separately packaged flexible dental treatment strips packaged with the sealed package as a kit so that individual dental treatment strips may be individually used with the exoskeleton body during placement on a person's teeth.

15. A method of applying a treatment composition to a person's teeth, comprising:

providing a dental treatment system comprising:

a generally flat, elongated dental treatment strip which is thin and flexible, and which is coated with a sticky or adhesive treatment composition so that when placed onto a portion of a person's upper or lower dental arch the treatment composition will hold the strip against the teeth in the absence of heating it to form it, or placing any other structure over it:

an exoskeleton body that is comprised of a flat, curved wall so as to approximate the curvature of a person's upper or lower dental arch, the exoskeleton body including an inner surface of the flat, curved wall that is oriented towards a person's tooth surfaces when used to place the dental treatment strip onto a person's teeth, and an outer surface oriented away from the person's tooth surfaces during placement of the dental treatment strip; and means for temporarily holding or attaching the flexible dental treatment strip to the inner surface of the flat, curved wall of the exoskeleton body until the dental treatment strip is placed onto a portion of the person's teeth, so that thereafter the dental treatment strip will be held to the teeth without any other structure while the exoskeleton body is removed from the dental treatment strip placing the dental treatment strip over at least a portion of the person's teeth; and separating the exoskeleton body from the dental treatment strip.

* * * * *